United States Patent
Essen-Moller

[11] Patent Number: 5,848,965
[45] Date of Patent: Dec. 15, 1998

[54] METHOD AND A SYSTEM FOR THE DETERMINATION OF PH AND OTHER FLUID PARAMETERS UTILIZING A METAL MONOCRYSTALLINE ELECTRODE

[75] Inventor: Anders Essen-Moller, Stockholm, Sweden

[73] Assignee: Synectics Medical AB, Stockholm, Sweden

[21] Appl. No.: 682,561

[22] PCT Filed: Jan. 24, 1994

[86] PCT No.: PCT/SE95/00072

§ 371 Date: Nov. 13, 1996

§ 102(e) Date: Nov. 13, 1996

[87] PCT Pub. No.: WO95/19733

PCT Pub. Date: Jul. 27, 1995

[30] Foreign Application Priority Data

Jan. 24, 1994 [SE] Sweden ................................. 9400204

[51] Int. Cl.[6] .............................. A61B 5/00; G01N 27/30
[52] U.S. Cl. ...................... 600/350; 600/353; 600/355; 600/361; 204/403
[58] Field of Search ...................................... 128/632, 635; 204/403, 412; 436/68; 600/345, 348, 349, 350, 353, 355, 361

[56] References Cited

U.S. PATENT DOCUMENTS

| | | | |
|---|---|---|---|
| 3,923,626 | 12/1975 | Niedrach et al. | 128/635 |
| 4,119,498 | 10/1978 | Edwall et al. | |
| 4,409,980 | 10/1983 | Yano et al. | |
| 4,816,131 | 3/1989 | Bomsztyk | 128/635 |
| 4,893,625 | 1/1990 | Schuhmann | |
| 5,126,937 | 6/1992 | Yamaguchi et al. | 128/635 |
| 5,158,083 | 10/1992 | Sacristan et al. | |

FOREIGN PATENT DOCUMENTS 9214398 9/1992 WIPO.

*Primary Examiner*—Jennifer Bahr
*Assistant Examiner*—Eric F. Winakur
*Attorney, Agent, or Firm*—Dowell & Dowell, P.C.

[57] ABSTRACT

A method and system for the determination of the pH of a fluid by measuring the pH of the fluid and thereafter correcting the pH based upon the determination of measured and/or adjusted values of at least one other parameter, such as $PO_2$ and $PCO_2$, which relate to the fluid.

20 Claims, 2 Drawing Sheets

METHOD AND A SYSTEM FOR THE DETERMINATION OF PH AND OTHER FLUID PARAMETERS UTILIZING A METAL MONOCRYSTALLINE ELECTRODE

BACKGROUND OF THE INVENTION

The present invention relates to a method for measuring by means of at least one electrode, such as an ambulatory measuring, the pH-value in the gastrointestinal tract.

The invention also relates to a system to perform such a method.

Units for the ambulatory registration for medical purposes are already known. Such a unit is known as Synectics MicroDigitrapper for the measuring of the pH-value, the $PO_2$ content and further such parameters. Several units also exist for measuring only the pH-value in different regions of the gastrointestinal tract. Such a unit is Synectics ED Digitrapper™ and Synectics ED Digitrapper MkII™. The sensor for the pH-value usually being applied are based on glass electrodes from Ingold, Switzerland and electrodes with an antimony crystal from Synectics according to USEA∃4,119, 498. Said publication describes an electrode for measuring the pH-value, and the $PO_2$- and $PCO_2$-content in fluids. The known methods for measuring the pH-value, however, are presenting essential measuring errors in certain measuring situations, e.g. in respect to measurements in the gastrointestinal tract.

SUMMARY OF THE INVENTION

The present invention provides the possibility to essentially improve the measuring accuracy in determinating e.g. the pH-value by means of monocrystal metallic electrodes.

The invention thus relates to a method according to the preambles of the attached claim 1. The method is especially characterized in what is stated in the characterizing part of said claim.

Moreover, the invention relates to a system according to the preambles of the attached claim 9. The system is especially characterized in what is stated in the characterizing part of said last mentioned claim.

The invention is described herein below with reference to execution examples and to the attached drawings, in which

DESCRIPTION OF THE PREFERRED EMBODIMENT

Figure 1:
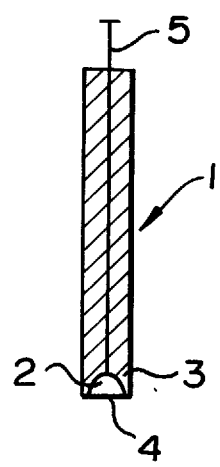
FIG. 1 shows schematically an axial section of a rodlike monocrystal electrode.

In FIG. 1 a metal monocrystal electrode is designated 1 generally according to the previously mentioned U.S. patent, the metal preferably being antimony, a crystal 2 of the metal being arranged to be exposed at the end 3 of the electrode and the plane crystal surface 4 adapted to be exposed to a fluid coinciding with a certain crystallographic constellation of the crystal. By means of a conductor 5 the crystal is coupled to an electric circuit. Between a reference electrode 6, FIG. 2, and the measuring electrode a potential difference is created under certain conditions and the electrode can be used to measure the pH-value, and the $PO_2$- and $PCO_2$-content. According to one embodiment the determination of the pH-value is to be perform by means of the measuring electrode 1. According to a special embodiment, FIGS. 3 and 4, the electrode is adapted and provided to be lowered into the gastrointestinal tract 8 of a patient 9, e.g. by means of a catheter 7, for an ambulatory and continuous determination of the pH-value in the gastrointestinal tract, a portable unit 10 being provided for the registeration of certain variables.

Measuring values related to the pH-value are meant to be corrected for the oxygen influence in the fluid within the actual measuring region, the oxygen content there being expressed as the partial pressure related to $O_2$ and is here expressed in that way, and means being provided for the determination of even $PO_2$ to be described further down.

By means of a counter 11, which preferably is comprised in the registration unit 10, the measuring result of the pH-value are meant to be corrected based on preferably generally all obtained measuring values related to $PO_2$, e.g. according to an empirically determined correlation:

$$pH_{corr} = pH_{read} \times K \times \frac{1}{1 - (PO_2 normal - PO_2 actual)}$$

where $pH_{cor}$ = corrected pH – value $pH_{ead}$ = measurd pH – value $PO_2 actual$ = measuring value related to $PO_2$ $PO_2 normal$ = mormal x value related to $PO_2$ K = a constant.

Also other correlations can possibly be provided for the correction, the correction correlation then preferably being adapted to the actual measuring environment and the actual variables of the integral parameters.

According to an embodiment the $PO_2$ is determined preferably by digital sensors 12, e.g. from Catalyst Research, the measuring being primarily related to the $PO_2$ in the blood, with the measuring based on transillumination, with the thus determined $PO_2$ being possibly correlated to the $PO_2$ in the measuring region.

Figure 2:
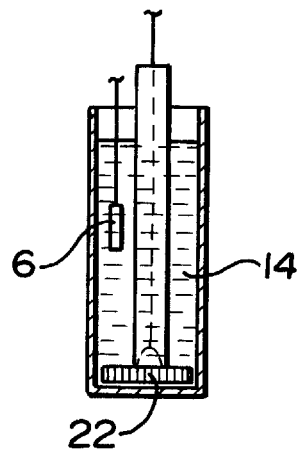
FIG. 2 shows schematically an arrangement of electrodes with reference bag and a reference electrode.
Figure 3:
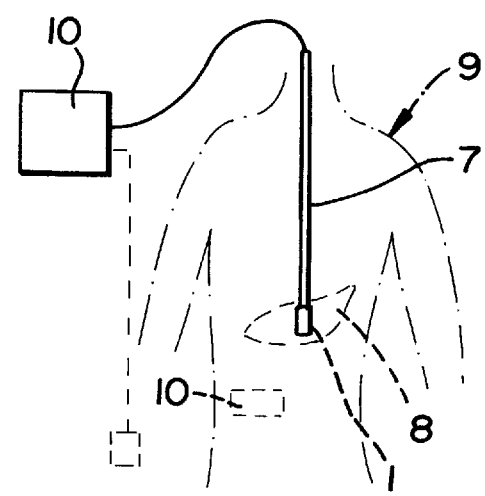
FIG. 3 shows schematically the ambulatory measuring according to the invention of e.g. the pH-value in the gastrointestinal tract.
Figure 4:
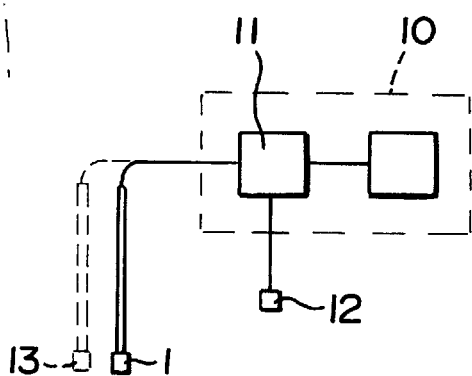
FIG. 4 shows schematically a first embodiment of a system according to the invention with two monocrystal electrodes.

According to another embodiment, FIG. 4, there is provided a further monocrystal electrode 13 for the determination of $PO_2$, the electrode preferably being of the same type as in the U.S. patent, FIG. 2, and comprising a buffer solution 14 as a reference solution for the determination of $PO_2$, regardless of the pH-value in the fluid in accordance with the description in the patent.

Figure 5:
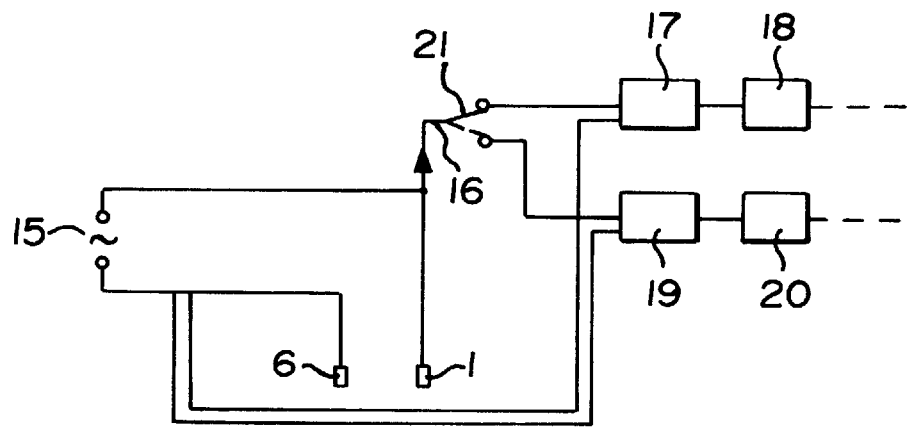
FIG. 5 shows schematically a second embodiment of a system according to the invention with two variables are determined with one single monocrystal electrode and two different circuit designs.

According to a further, preferred embodiment, FIG. 5, the measuring electrode for the pH-value is also adapted to be used for the determination of $PO_2$, various different electrical circuits being provided for the determination of the pH-value and the determination of $PO_2$. According to the illustrated embodiment i.a. the measuring electrode is connected to a voltage source 15 adapted to provide a voltage with an AC-component, the voltage preferably not being the same for the determination of the pH-value and the determination of $PO_2$. The output signal 16 from the circuit in the configuration for the determination of the pH-value is sent to a pH-value amplifier 17 and means 18 of a convenient design for the analysis of preferably both the amplitude and the phase condition for a separation of the pH-values. In a corresponding way the output signal 16 is transmitted from the circuit in the configuration for the determination of $PO_2$ to a $PO_2$-amplifier 19 and means 20 of a convenient design for the analysis of preferably both the amplitude and the phase condition for a separation of the $PO_2$-values. There are also means 21 for an alternating between said configuration for the determination.

Figure 6:
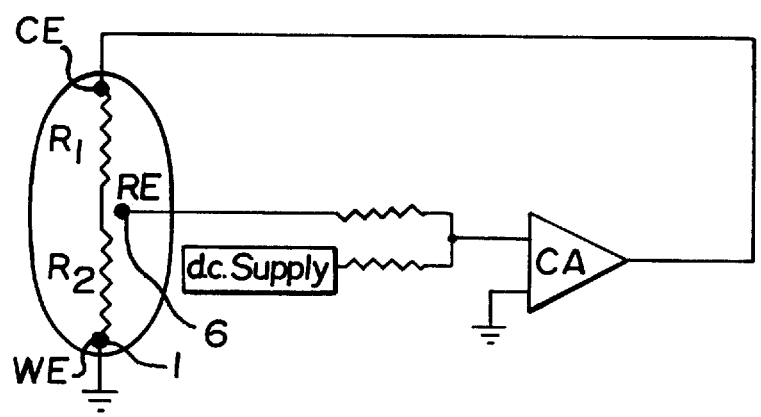
FIG. 6 shows schematically a monocrystal measuring electrode arranged within a potentiostat with a counter electrode.

According to a further embodiment with the same electrode 1 for several variables, FIG. 6, a potentiostat arrangement is used, the counter resistor CE of the potentiostat is adapted and provided to be varied using control means CA to vary the voltage. The potentiostat is then arranged in such a way that during a change of the counter electrode voltage and even the frequency, with which the counter electrode voltage is changed, it becomes possible to separate any components which are specific for the pH-value, and the $PO_2$- and $PCO_2$-content, e.g. a double layer capacitance and a charging transmission resistance, kinetic constants possibly to be calculated and related to measuring variables, i.e. the concentrations of the corresponding substance, i.e. the pH, the $PO_2$ and the $PCO_2$. For a further information of the potentiostat and the measuring procedures here is referred to *Bioelectronics—Principles of Bioenergetics and Bioelectrochemistry*, Oxford Press, 1990, especially pages 33–37.

According to a further embodiment there is also provided a fluid impermeable diaphragm 22 provided with a monocrystal electrode, FIG. 2, for the determination of $PCO_2$, even the $PCO_2$ being in applicable cases adapted to form the basis for a correction of the determination of the pH-value.

The method and the function of the system according to the invention has been generally clarified in the description above. A measuring with a monocrystal electrode is thus supplemented by a measuring of at least one further parameter with simultaneously mutually dependent parameters, such as the pH-value and the $PO_2$, the measuring result being corrected on the basis of the performed determination and the correction relation stated for the actual parameters.

Thus, the invention provides a possibility to use metal monocrystal electrodes with an essentially improved accuracy, which already are providing extremely accurate measuring.

The invention has been described above with reference to execution examples. Further embodiments can of course be imagined as well as smaller changes and supplements without leaving the scope of the invention.

The invention is also applicable for other types of electrodes besides metal monocrystal electrodes, and in the case of metal electrodes the invention is applicable even for polycrystal and amorph metal electrodes and not only for monocrystal electrodes.

Moreover, other circuitries than the already described ones can possibly be used for embodiments using various electric circuitries for the determination of the pH-value and of the $PO_2$ with the same electrode, the electrode then in most cases being electrically energized in different ways during the corresponding determination as a result of the various circuitries. Embodiments using various circuitries for different parameters with the same electrode are also applicable to other parameters than $PO_2$ and the pH-value.

Therefore, the invention is not limited to the already above state embodiments but can be varied within the scope of the attached claims.

I claim:

1. A method for determining the pH of a fluid using a metal monocrystalline electrode comprising the steps of:
    a. measuring the pH of the fluid by exposing the metal monocrystalline electrode to contact with the fluid while connecting the electrode to a power supply source and a means for analyzing signals received from the electrode to obtain a measured pH value of the fluid;
    b. measuring at least one further parameter relating to the fluid to determine a measured value for said at least one further parameter; and
    c. determining a corrected pH value of the fluid by adjusting the measured pH value of the fluid based upon the measured value of said at least one further parameter.

2. The method of claim 1 wherein the step of measuring at least one further parameter includes measuring a parameter selected from the group consisting of $PO_2$ and $PCO_2$.

3. The method of claim 2 including the additional steps of inserting the metal monocrystalline electrode into the gastrointestinal tract of a patient so that said metal monocrystalline electrode is in contact with the gastrointestinal fluid and wherein said step of measuring the pH of the fluid is done while the patient is ambulatory.

4. The method of claim 1 wherein the step of measuring at least one further parameter includes measuring a $PO_2$ value of the fluid.

5. The method of claim 4 including the additional steps of inserting the metal monocrystalline electrode into the gastrointestinal tract of a patient so that said metal monocrystalline electrode is in contact with the gastrointestinal fluid and wherein said step of measuring the pH of the fluid is done while the patient is ambulatory.

6. The method of claim 5 wherein the step of measuring the $PO_2$ includes connecting the electrode to the power supply source and means for analyzing signals received from the electrode to obtain a measured $PO_2$ value.

7. The method of claim 6 wherein power supplied to the electrode includes an AC voltage component which is of one value when measuring the pH of the fluid but which is another value when measuring the $PO_2$ value.

8. The method of claim 4 wherein the step of measuring the $PO_2$ value includes measuring the $PO_2$ value of the fluid utilizing a second monocrystalline electrode and adjusting the measured value utilizing a reference value received by measuring a buffer solution to provide a normal $PO_2$ value independent of the measured pH value of the fluid.

9. The method of claim 8 including the additional steps of inserting the metal monocrystalline electrode into the gastrointestinal tract of a patient so that said metal monocrystalline electrode is in contact with the gastrointestinal fluid and wherein said step of measuring the pH of the fluid is done while the patient is ambulatory.

10. The method of claim 8, including the additional step of connecting the metal monocrystalline electrode to a potentiostat to thereby vary the voltage thereto dependent upon a parameter being measured.

11. The method of claim 4 wherein the method of measuring the $PO_2$ value includes measuring a value of $PO_2$ in blood of a patient with a sensor for measuring the $PO_2$ value in the blood and correlating the value of $PO_2$ in blood to the $PO_2$ value of fluid.

12. The method of claim 11 including the additional steps of inserting the metal monocrystalline electrode into the gastrointestinal tract of the patient so that said metal monocrystalline electrode is in contact with the gastrointestinal fluid and wherein said step of measuring the pH of the fluid is done while the patient is ambulatory.

13. A system for determining the pH of a fluid by initially measuring the pH value of the fluid and thereafter determining a corrected pH value by adjusting the measured pH value based upon the measurement of at least one further parameter of the fluid, the system comprising: at least one metallic monocrystalline electrode adapted to be contacted with the fluid, a first electrical circuit connecting the at least one electrode between a source of power and means for analyzing an output from at least one electrode to measure the pH value of the fluid, and means for determining the value of the at least one other parameter of the fluid to obtain a parameter value of the at least one other parameter and means for obtaining the corrected pH value of the fluid by adjusting the measured pH value of the fluid based upon the parameter value of the at least one parameter.

14. The system of claim 13 wherein said at least one electrode is mounted to a catheter adapted to be inserted into a gastrointestinal tract of a patient.

15. The system of claim 14 in which said means for determining the value of said at least one parameter of the fluid includes a second electrical circuit connected to said at least one electrode, said second electrical circuit being connected between said source of power and means for analyzing the $PO_2$ value of the fluid based upon another output of said first electrode.

16. The system of claim 15 including a reference electrode mounted within a buffer solution, said reference electrode being connected to a source of power and by another electrical circuit to said means for analyzing the $PO_2$ value.

17. The system of claim 16 including a potentiostat electrically connected to said first electrode, said potentiostat including a counter electrode, and means for varying the voltage to said counter electrode.

18. The system of claim 15 in which said source of power is variable and adapted to provide an AC voltage component, further including switch means connected between said first electrode and said means for analyzing the pH value and means for measuring the $PO_2$ value so that different voltages are applied to said means for measuring said pH value and said means for measuring said $PO_2$ value.

19. The system of claim 14 wherein said means for determining the value of at least one other parameter includes a digital sensor for measuring $PO_2$ parameter in blood of the patient to thereby obtain a correlated value of $PO_2$ in the fluid.

20. The system of claim 13 wherein said at least one monocrystalline electrode is an antimony monocrystalline electrode.

* * * * *

UNITED STATES PATENT AND TRADEMARK OFFICE
CERTIFICATE OF CORRECTION

PATENT NO. : 5,848,965
DATED : Dec. 15, 1998
INVENTOR(S) : Anders Essen-Moller

It is certified that error appears in the above-identified patent and that said Letters Patent is hereby corrected as shown below:

On the title page, item [22]:

Please delete "Jan. 24, 1994" and insert --Jan. 24, 1995--.

Signed and Sealed this

Twenty-seventh Day of July, 1999

Attest:

Q. TODD DICKINSON

*Attesting Officer*                *Acting Commissioner of Patents and Trademarks*